United States Patent [19]

Sakita et al.

[11] Patent Number: 4,981,143
[45] Date of Patent: Jan. 1, 1991

[54] CELL SAMPLER

[75] Inventors: Hirofumi Sakita, Machida; Takuji Ikesue, Chiba, both of Japan

[73] Assignee: Anne Company Limited, Isehara, Japan

[21] Appl. No.: 86,255

[22] Filed: Aug. 13, 1987

Related U.S. Application Data

[63] Continuation of Ser. No. 853,223, Apr. 17, 1986, abandoned.

[30] Foreign Application Priority Data

Apr. 20, 1985 [JP] Japan .................................. 60-85229

[51] Int. Cl.⁵ ............................................ A61B 10/00
[52] U.S. Cl. ..................................................... 128/757
[58] Field of Search ................ 128/749, 751, 756–758, 128/304; 604/22, 46, 47, 54

[56] References Cited

U.S. PATENT DOCUMENTS

| | | | |
|---|---|---|---|
| 865,571 | 9/1907 | Currey | 128/304 |
| 2,495,794 | 1/1950 | Weller | 128/757 |
| 2,514,665 | 7/1950 | Myller | 128/757 |
| 2,583,750 | 1/1952 | Runnels | 128/304 |
| 2,677,843 | 5/1954 | Goodman | 128/304 |
| 2,835,246 | 5/1958 | Boettger | 128/757 |
| 2,955,592 | 10/1960 | MacLean | 128/756 |
| 3,308,825 | 3/1967 | Cruse | 128/757 |
| 3,540,432 | 11/1970 | Ayre | 128/758 |
| 3,592,186 | 7/1971 | Oster | 128/757 |
| 3,732,869 | 5/1973 | Bronstein | 128/304 |
| 3,838,681 | 10/1974 | Dalton | 128/757 |
| 4,027,658 | 6/1977 | Marshall | 128/757 |
| 4,054,127 | 10/1977 | Milan et al. | 128/757 |
| 4,243,049 | 1/1981 | Goodale et al. | 128/757 |
| 4,361,948 | 12/1982 | Omata | 128/756 |
| 4,384,587 | 5/1983 | Milgrom | 128/757 |
| 4,562,847 | 1/1986 | Nydahl et al. | 128/757 |

OTHER PUBLICATIONS

"Gynecological Instruments", Novak, Surgical Instruments, 1973.

Primary Examiner—Max Hindenburg
Attorney, Agent, or Firm—Oblon, Spivak, McClelland, Maier & Neustadt

[57] ABSTRACT

A cell sampler obtaining specimens of cells for cytodiagnosis comprises stick-shaped handle which has at one end thereof a stick-shaped abrading segment with a multiplicity of edges formed around the periphery thereof for the purpose of scraping off cells from the cervical canal of the uterus.

Such cell sampler enable, with ease and certainly, to obtain cells from the cervical canal for cytology by scraping off with edges thereon.

10 Claims, 4 Drawing Sheets

CELL SAMPLER

This application is a continuation of application Ser. No. 853,223, filed on Apr. 17, 1986, now abandoned.

BACKGROUND OF THE INVENTION

1. Field of the Invention

This invention relate's to a cell sampler designed to obtain specimens cf cells for use in the cytology of cancer of the cervix and the like.

2. Description of the Prior Art

Recently the incidence of uterine cancer has been steadily increasing. Of vital importance for the prevention of this disease is the early detection through periodical checkups.

Such examination of uterine cancer, especially that of uterine cervix, is carried out by collecting specimens of cells from the cervix and cervical canal of the uterus using a cell sampler. Application of cytology to the cervical canal is particularly effective for the discovery of early or incipient cancer in that portion. Occurring in basal and/or para-basal cells at a depth of 100 to 300 $\mu$m, cancers in the cervix uterine areas gradually spread into intermediate and surface cells at a depth of 30 to 100 $\mu$m. To ensure the early detection of such cancers, therefore, sampling of cells from the above-mentioned portions, especially basal and para-basal cells, in a sure way is indispensable.

Heretofore, several types of cell samplers have been used for the above purpose, such as a swab shown in FIG. 14, a spatula shown in FIG. 15 and a brush shown in FIG. 16. However, such conventional tools are known to have the following drawbacks.

A. Swab (a) Because the wad of cotton is so soft and so apt to get moistened by secretions that the swab does not have large enough abrasive force to enable the collection of cell specimens from the whole of epithelium. When too much force is applied, the stick may break and expose the subject to a great danger.

(b) Large quantities of secretions and other unnecessary stuffs are likely to be collected together with the desired cells. This mixing calls for an extra time-consuming step of separation before the specimen becomes ready for microscopic examination.

(c) Collected cells are likely to coil around the cotton wad. Once thus entwined, they are difficult to remove and, therefore, smear on a slide glass.

B. Spatula (a) Although suited for mass sampling, the spatula tends to scrape off an aggregate of tissues containing unnecessary cells such as interstitial ones. In many instances, cells in such aggregates heavily overlap each other. So, individual cells are difficult to distinguish from each other, thereby making it difficult to render correct judgement.

(b) The risk of causing abrasion and bleeding at the sampling spot is great.

(c) The spatula is unsuited for the most important task of cell sampling from the cervical canal.

C. Brush (a) Having a sharply pointed end, the brush involves a great danger of injuring the subject.

(b) Collected cells are apt to fall off from the bristles when the brush is taken away from the cervical canal.

(c) Collected cells cannot be smeared on a slide glass unless the bristles are forcibly pressed thereagainst for squeezing. This task requires considerable practice and expertness.

SUMMARY OF THE INVENTION

A primary object of this invention is to provide a cell sampler designed to obtain, with ease and certainty, cells, particularly those from the cervical canal of the uterus, for cytology by scraping off with the edges thereon.

Another object of this invention is to provide a cell sampler of the versatile type that is applicable to a large number of subjects whose shape of vaginal and uterine canal can vary considerably from person to person.

Still another object of this invention is to provide a cell sampler that is safe in use, with the risk of injuring the sampling area being eliminated.

Yet another object of this invention is to provide a cell sampler that is capable of surely collecting cells from such depths where incipient cancer can be found effectively.

A further object of this invention is to provide a cell sampler that securely holds the collected cells and permits them to be readily smeared onto a slide glass.

A still further object of this invention is to provide a cell sampler that is made of synthetic resin with simple design and at low cost, with the abrading edges provided around the periphery of the projected and indented portions thereof.

For achieving the above objects, a cell sampler according to our invention has a stick-shaped abrading segment having a number of edges adapted to scrape off cells from the cervical canal of the uterus around the periphery thereof, with the abrading segment attached to one end of the stick-shaped handle that has a shape of a small-diameter stick.

The above cell sampler of this invention is adapted to scrape off cells from the cervical canal of the uterus and so on with many small edges provided around the periphery of the stick-shaped abrading segment thereof. Accordingly, the cells in the desired spot can be collected safely and with certainty by simply turning or axially moving the sampler.

The above and other objects, structures and effects of this invention will be made explicit in the following detailed description of preferred embodiments which is to be read in conjunction with the accompanying drawings. It goes without saying that the examples described are given only to illustrate certain perferred embodiments of this invention to which the invention is by no means limited.

DESCRIPTION OF THE PREFERRED EMBODIMENTS

The invention is further illustrated by giving some examples designed for the cytodiagnosis of uterine cancer.

Figure 1:
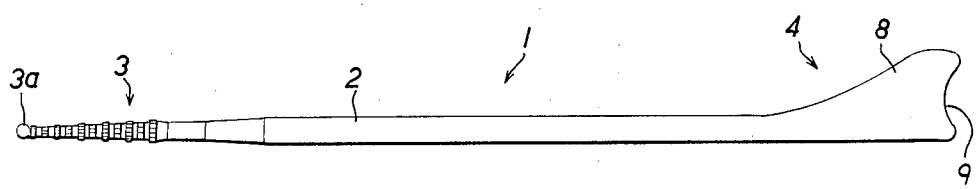
FIG. 1 is a front view of a preferred embodiment of this invention.

FIG. 1 shows a first preferred embodiment of this invention. A sampler 1 comprises a stick-shaped handle 2 of small diameter having a circular or square cross section, with a stick-shaped abrading segment 3 and a spatula-shaped abrading segment 4 provided at one end of the handle the other end thereof. The whole implement is integrally made of synthetic resin.

Figure 2:
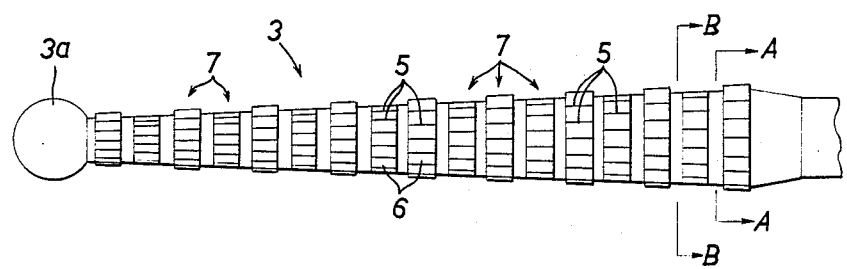
FIG. 2 is the front view enlarging the principal portion of the same embodiment.
Figure 3:
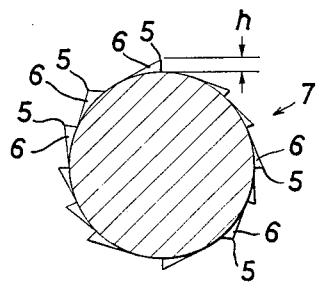
FIGS. 3 and 4 are the cross-sectional views taken along the lines A—A and B—B in FIG. 2, respectively.
Figure 4:
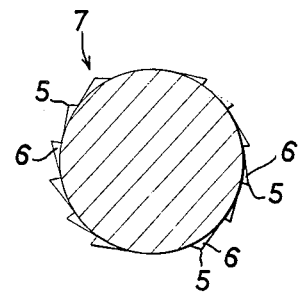

The stick-shaped abrading segment 3 is intended for scraping off cells from the cervical canal of the uterus. As is fully illustrated in FIGS. 2 to 4, the proximal end of the abrading segment 3 is attached to the handle and is made to such a size as can be inserted into the cervical canal without causing pain to the subject. The segment 3 is also tapered like an elongated circular cone or pyramid, with a reduced width at the distal end 3a so as to cope with the differences in the shape of the examined portion among individuals. Fine edges 5 to scrape off cells are provided around the periphery of many projections 6 formed thereon.

The projections 6 on the periphery of the abrading segment may be formed in various shapes. The preferred embodiment being described has a multiplicity of saw-tooth-like projections 6 formed around the circumference of a circle. The edges 5 constitute an array 7 of projections directed in the same direction (e.g., clockwise as on the illustrated preferred embodiment) like the teeth of a ratchet. Several arrays 7 of projections are provided at intervals along the axis of the abrading segment 3, with the projections 6 on the adjoining arrays 7 being circularly staggered. To insure safety, the distal end 3a of the abrading segment 3 is spherically shaped.

For collecting cells, the stick-shaped abrading segment 3 is inserted into the cervical canal. Then, cells are scraped off with the edges 5 thereon by turning the sampler 1 in the direction in which the edges 5 are set (clockwise). To ensure that both surface and basal cells are surely collected without damaging the stroma, the height of the edges 5 should preferably be set between 30 $\mu$m and 500 $\mu$m, or more particularly between 50 $\mu$m and 350 $\mu$m.

Having a practically roughened surface covered with many projections 6, the abrading segment 3 securely holds the collected cells. So few cells fall off when the sampler 1 is pulled out from the cervical canal.

The collected cells are readily smeared onto a slide glass by turning the sampler 1 in a direction (counterclockwise) opposite to that in which it was turned for sampling.

Although the space between the projections 6 and the angle of the edges 5 are varied circumferentially on the illustrated preferred embodiment, they may also be made equal throughout.

On the other hand, spatula-shaped abrading segment 4 at the other end of the stick-shaped handle 2 is intended for collecting cells from the posterior vaginal fornix or uterovaginal canal. The embodiment shown in FIG. 1 is engineered for the uterovaginal canal. A flattened segment 8 has an indentation 9 at the tip thereof which is shaped to conform to the contour of the cervical canal. For collecting cells from the cerval canal, the indentation 9 held thereagainst is rubbed therealong, as with a spatula of the known type.

The sampler 1 may be made of metal or other suitable materials. One of preferable material is synthetic resin. Especially, polyolefin resins such as polyethylene, polypropylene, vinyl acetate copolymers and ethylene vinyl alcohol copolymers, polystyrene resins such as polystyrene and acrylonitrile butadiene styrene (ABS), polyamide and olefin vinyl alcohol copolymers insure firm adherence and easy transfer of cells onto a slide glass.

To further facilitate the adherence of cells, the entire surface of the abrading segments 3 and 4 may be roughened with fine ruggedness.

Also, the edges 5 in the stick-shaped abrading segment 3 may be circumferentially directed in opposite directions on adjoining arrays 7 of projections. By so doing, easier sampling is possible, with the directionality in manipulation eliminated.

Figure 5:
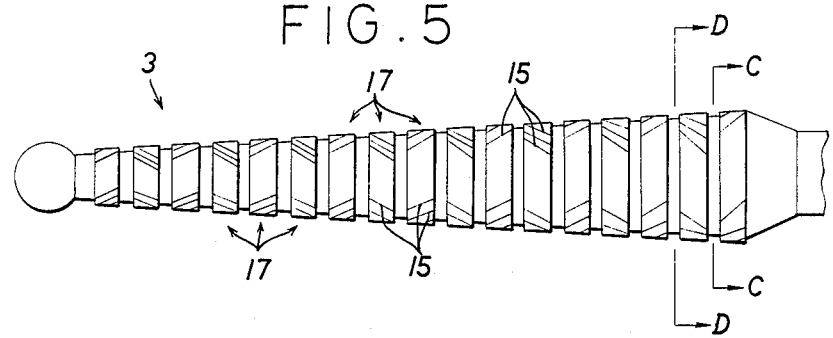
FIGS. 5 to 7 are front views showing the principal portion of the stick-shaped abrading segment of another embodiment, and the cross-sectional views taken along the lines C—C and D—D therein.
Figure 6:
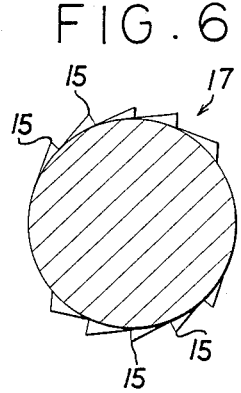
Figure 7:
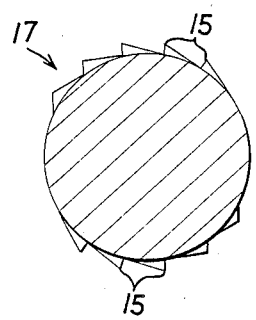

FIGS. 5 to 7 show another type of edges in the stick-shaped abrading segment 3. Edges 15 are not only slanted with respect to the axis of the abrading segment 3 but also circumferentially oppositely directed on adjoining arrays 17 of projections. Of course, the edges 15 on the individual arrays 17 of projections may be directed in the same direction, as well.

Figure 8:
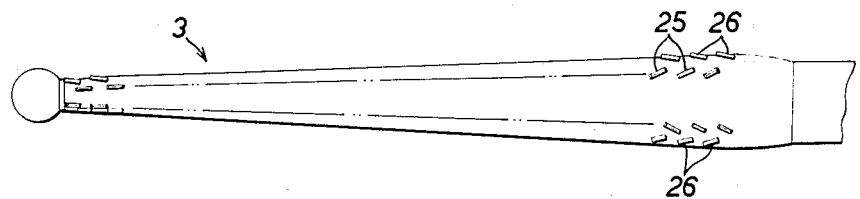
FIGS. 8 and 9 are front views of the stick-shaped abrading segment of other embodiments.

FIG. 8 illustrates another preferred embodiment in which a multiplicity of triangular-prism-like projections 26 slanted with respect to the axis of the stick-shaped abrading segment 3 are axially and circumferentially provided at intervals, with an edge 25 formed at the ridge of each projection. Circumferentially adjoining projections 26 or edges 25 are oppositely slanted. Furthermore, the projections 26 are slanted progressively less sharply toward the tip of the abrading segment 3.

With this type of provision, cells can be collected by not only turning around but also axially moving back and forth a sampler.

The shape, direction and other design parameters of the projections and edges in the stick-shaped abrading segment 3 are by no means limited to those of the above preferred embodiments but may be varied randomly. Instead of forming such projections, grooves may be cut to form edges along the edge thereof. In short, the stick-shaped abrading segment 3 according to this invention can serve the purpose thereof so long as edges are formed at the ridge of projections, grooves or indentations provided along the periphery thereof.

Figure 9:
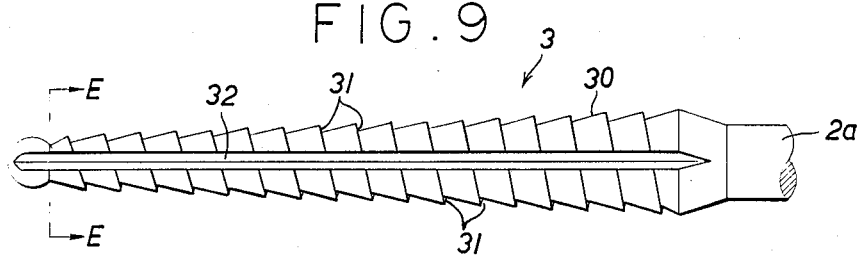
Figure 10:
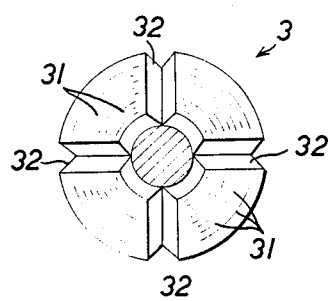
FIG. 10 is a cross-sectional view taken along the line E—E of FIG. 9.

FIGS. 9 and 10 show yet another preferred embodiment having a spiral groove 30 superimposed on the elongate tapered form of the abrading element by being cut in the stick-shaped abrading segment 3 thereof. Cell-scraping edges 31 directed toward the handle 2a i.e., towards the proximal end of the abrading element are formed at the edge of the spiral groove 30. Four equally spaced longitudinal grooves 32 are axially cut in the stick-shaped abrading segment as well.

Figure 11:
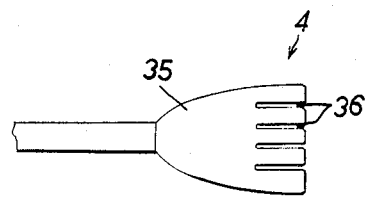
FIG. 11 is a front view of the spatula-shaped abrading segment of still another embodiment.

FIG. 11 shows the spatula-shaped segment 4 of another preferred embodiment. Two or more slits 36 are cut in the tip of a flattened flexible piece to increase the fitness to the sampling spot.

Figure 12:
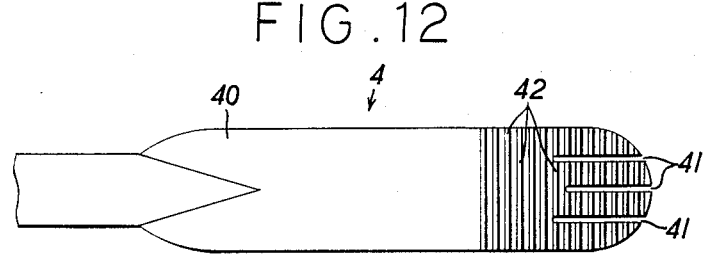
FIGS. 12 and 13 are a front view and a side elevation of the spatula-shaped abrading segment of yet another embodiment.
Figure 13:
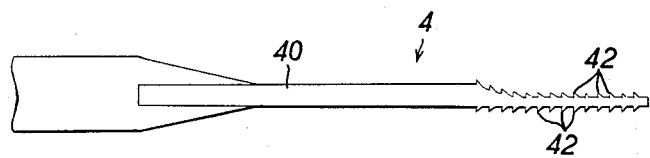
Figure 14:
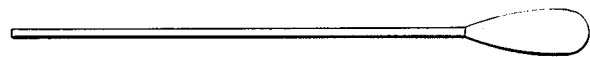
FIGS. 14 to 16 are front views of conventional cell samplers.
Figure 15:
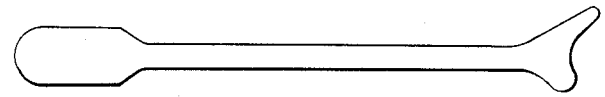
Figure 16:

Finally, a spatula-shaped abrading segment 4 shown in FIGS. 12 and 13 has a flattened portion 40 having slits 41, with the tip thereof being reduced in thickness. The thinned portion has more than one ribs 42 on the top and bottom sides thereof, and each rib 42 has a triangular cross section and extends in a direction perpendicular to the axis of the stick-shaped handle.

What is claimed is:

1. A cell sampler comprising:
   a stick shaped handle having two ends; and
   a first abrading segment at one of said ends, said first abrading segment comprising:
   (a) an elongate form having a proximal end fixed to said handle and tapering with a reduced width to a distal end thereof to aid in insertion of said cell sampler into a body cavity to be sampled,
   (b) means for defining at least one spiral superimposed on said elongate tapering form from said distal end to said proximal end, said at least one spiral having edges facing said proximal end; and
   (c) a plurality of longitudinal grooves formed in said first abrading segment,
   whereby said spiral and said longitudinal grooves facilitate the collection of cells.

2. The cell sampler of claim 1, wherein said elongate form is pyramidal.

3. The cell sample of claim 1, wherein said elongate form is conical.

4. The cell sampler of claim 1, wherein said edges having a height of between 30 $\mu$m and 500 $\mu$m.

5. The cell sample of claim 1, including a second abrading segment attached to another of said ends, said second abrading segment being spatula shaped.

6. The cell sample of claim 5 unitarily formed of synthetic resin.

7. The cell sampler of claim 5, wherein the surface of at least one of said abrading segments is roughened.

8. The cell sampler of claim 1, wherein said grooves are equally circumferentially spaced.

9. The cell sampler of claim 1 unitarily formed of synthetic resin.

10. The cell sampler of claim 1 wherein the surface of said first abrading segment is roughened.

* * * * *